United States Patent [19]

Jitsukawa

[11] Patent Number: 4,931,400
[45] Date of Patent: Jun. 5, 1990

[54] DEVICE FOR POURING WASHING WATER ONTO MUTI-WELL PLATES

[75] Inventor: Tomofumi Jitsukawa, Saitama, Japan

[73] Assignee: Hoechst Japan Limited, Tokyo, Japan

[21] Appl. No.: 234,045

[22] Filed: Aug. 19, 1988

[30] Foreign Application Priority Data

Aug. 22, 1987 [JP] Japan .................................. 62-127929

[51] Int. Cl.$^5$ .............................................. C12M 1/22
[52] U.S. Cl. .................................... 435/287; 435/293; 134/169 R; 134/196; 222/215; 222/330; 422/100
[58] Field of Search ............... 435/300, 301, 311, 287, 435/293; 134/169 R, 196; 222/215, 330; 73/863.32; 422/100, 99; 141/237, 2, 23, 25, 26

[56] References Cited

U.S. PATENT DOCUMENTS

| | | | |
|---|---|---|---|
| 1,882,668 | 10/1932 | McCabe | 222/330 |
| 3,157,319 | 11/1964 | Schwienbacher | 222/215 |
| 3,785,928 | 1/1974 | Kessler | 435/287 |
| 4,072,249 | 2/1978 | Ekenstam et al. | 222/215 |
| 4,356,830 | 11/1982 | Holzapfel | 134/196 |
| 4,493,896 | 1/1985 | La Motte, III et al. | 435/287 |
| 4,496,657 | 1/1985 | Coppersmith et al. | 435/287 |
| 4,548,245 | 10/1985 | Crandell et al. | 222/330 |

Primary Examiner—James C. Yeung
Attorney, Agent, or Firm—Finnegan, Henderson, Farabow, Garrett, and Dunner

[57] ABSTRACT

A device for forcing liquid into the wells of a multi-well plate, comprising a tank having an interior for holding a liquid, the tank including a bottom portion having multiple fine orifices spaced for registry with each of the multiple wells of the plate, a top portion opposite the bottom portion, and side portions connecting the top portion and the bottom portion, an inlet for supplying rinsing liquid to the interior of the tank, and a pushable surface portion selectively movable towards the interior of the tank for forcing rinsing liquid contained within the tank through the orifices.

5 Claims, 1 Drawing Sheet

DEVICE FOR POURING WASHING WATER ONTO MUTI-WELL PLATES

BACKGROUND OF THE INVENTION

1. Field of the Invention

The present invention relates to a device for pouring washing water on to multi-well plates which are particularly used for assay of biological materials in clinical laboratories, in hospitals, and in biochemical laboratories.

2. Statement of the Prior Art

Clinical examinations in hospitals and like work involve the handling of a large number of samples within as short a time as possible. To this end there may be provided a plastic instrument having, for example, a total of 96 sample wells which are arranged in an array of 8×12 wells. This kind of plate having therein 96 wells is shaped to a certain standard size adapting to automated analyzers. The pouring of samples and reagents in to the wells, optical measurement, and other procedures are automatically carried out by the automated devices.

In case of an immunoassay called the enzyme-linked immunosorbent assay, it is required to wash wells a number of times, since the reaction takes place on the inner wall surfaces of wells. However, with some simplified type automated analyzers, manual washing must be carried out due to the absence of any washing step in the device. It is troublesome and time consuming to pour washing water into as many as 96 wells.

SUMMARY OF THE INVENTION

An object of the present invention is to solve such problems by providing a device capable of pouring washing water onto such a multi-well plate instantly and completely.

More specifically, the present device for pouring washing water onto a multi-well plate is characterized by a washing water tank which is to be placed on a multi-well plate to be washed, this washing water tank being constructed as follows.

(a) The washing water tank has in its bottom fine orifices for respectively confronting the wells in the multi-well plate;
(b) the washing water tank is tightly sealable, except for the orifices;
(c) the washing water tank has at least a part of its structural faces formed of an elastic synthetic resin material which is designed to be pressed to force the washing water contained inside through the orifices to the outside; and
(d) the washing water tank is so adapted that washing water can be supplied thereinto.

With a device constructed in accordance with the present invention, it is possible to wash respective wells in a multi-well plate simultaneously and repeatedly (until the washing water contained is used up). This is accomplished by pressing force applied by the fingers to a portion of the device formed of an elastic synthetic resin material. The applied force serves to eject the water simultaneously from the orifices into the respectively facing wells of the multi-well plate.

BRIEF DESCRIPTION OF THE DRAWINGS

A specific embodiment of the present invention will now be described, by way of example, with reference to the accompanying drawings in which.

DETAILED DESCRIPTION OF THE PREFERRED EMBODIMENT

Figure 1:
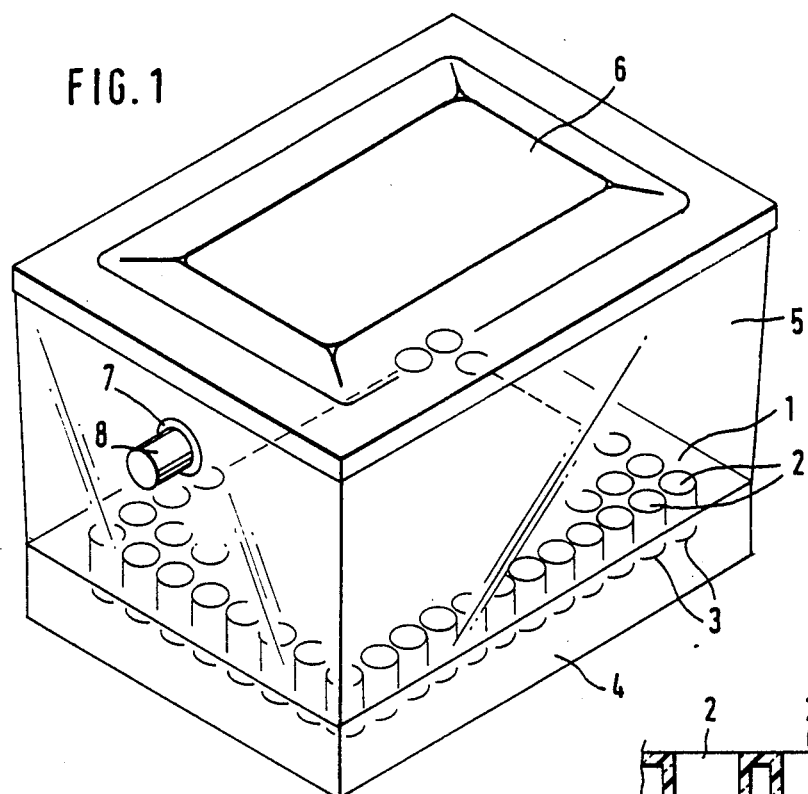
FIG. 1 is a perspective view of one example of the water-pouring device according to the present invention.

One specific embodiment of the washing water-pouring device according to the present invention includes a tank having a multiplicity of fine orifices its bottom. The orifices correspond with and respectively face a multiplicity of wells in a multi-well plate.

Since conventionally used multi-well plates are of rectangular shape in plan view, the bottom of a washing water tank to be placed thereon takes on a rectangular, more specifically, rectangular-parallelepipedic form (including a truncated quadrangular-pyramid form), correspondingly.

One example of such a washing water tank has a bottom (including therein such orifices as mentioned above) and sides formed of hard plastics which may be either transparent or semi-transparent, such as, in particular, polystyrene, polyvinyl chloride, polymethyl methacrylate, hard polyethylene and polypropylene.

According to an embodiment of the tank of the present invention, a top face of such a hard plastic tank as mentioned above is formed of an elastic synthetic resin material. This top face may be part of a detachable lid member that tightly fits on the tank. When the lid is on the tank, the tank is tightly sealed (except for the orifices provided in its bottom, as a matter of course). Such a lid member is formed of elastic plastics such as soft polyethylene and plasticized polyvinyl chloride. It is to be noted herein that the lid is formed of an elastic plastic material implies that the washing water contained in the tank is forced from the orifices to the outside by a force applied from the outside to said lid. The plastic material per se need not be soft. It is thus to be understood that satisfactory results are obtained if the lid member formed of the plastic material is made large in area or thin in thickness, whereby, upon being pressed, it yields to transmit pressure to the interior of the tank.

If the top face or lid of the tank is constructed as above, then the interior pressure of the tank is increased when the lid is pressed down by fingers, thereby making it possible to run the washing water through the bottom orifices into all of the wells in a multi-well plate at the same time. The magnitude of the elastic force of the top plastic material and the size of the bottom orifices are such that water does not drop from the orifices unless the top face is pressed down by fingers. In addition after the top face has been pressed down by fingers, air is admitted through the orifices into the tank to restore the top face to its original form. If the top face is defined by a lid mamber which is tightly closeable and removable, then cleaning can conveniently be carried out when the orifices are clogged.

The orifices in the bottom of the washing water tank may be provided in the flat bottom , the orifice corresponding with the wells in a multi-well plate. However, if orifices are formed in the lowermost portions of wells in a plate of a shape identical with or similar to that of a multi-well plate, it is then easy to obtain orifices corresponding to the wells in a multi-well plate. Since multi-well plates are usually designed to be stacked one over another, it is a matter of course that the respective wells in the multi-well plates can correspond to the bottom holes of the washing water tank (which have orifices formed in their lowermost portions). In such a case, it is desirable that a multi-well plate having wells with U-shaped cross-section be utilized for the bottom.

Since it includes the washing water tank, the washing water-pouring device of the present invention should be constructed in such a manner that washing water can be supplied thereto. One example of such a construction is that the top face of the tank is formed by a detachable lid member. In another example, a water inlet is provided in a suitable site of the tank, i.e., a site which will not be an impediment to placing the present device on a multi-well plate, more specifically, a side or top site of the tank. It is true that the former construction is simpler, but it offers a problem in that water must be supplied, while care is taken to prevent water leakage from the tank bottom. However, it is indeed possible to prevent water leakage through the orifices if a rubber sheet, as an example, if the sheet is held against the orifices during water supply. The provision of an exclusive water inlet is said to be advantageous in that water supply can be carried out as an independent step.

When the present device is placed over the flat face of a laboratory table, etc., water may drop if the orifices contact the table surface. It is therefore desired that side walls or a projecting skirt be formed around the bottom of the device. It is not desireable for the walls of the device to contact the circumference of the multi-well plate in an airtight manner. Therefore, it is preferable to provide a hole in order to not form an airtight region between the bottom of the device and the surface of the plate.

Referring now to the drawings, FIG. 1 is a perspective view of the pouring device using a multi-well plate having U-shaped wells. A bottom 1 is formed by a commercially available 96-well plastic plate having therein U-shaped wells 2, which are provided with orifices 3 in their lowermost portions. Side members 5, one of which is formed therein with a water inlet 7 together with a silicone rubber plug 8, are provided on the edge of the bottom 1 by laminating, etc. A top face 6 is formed by a removable but closeable lid. The bottom 1 includes a side wall 4 higher than the height of each U-shaped well, which serves to prevent water from dripping when the present device is placed on a laboratory table.

Figure 2:
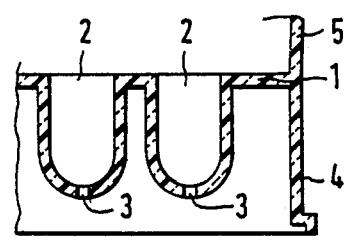
FIG. 2 is a relatively enlarged fragmentary view, in vertical section, of the bottom of water-pouring device of FIG. 1.

FIG. 2 is an enlarged sectional view showing the U-shaped wells 2, pores 3, side members 5 and side wall 4.

Figure 3:
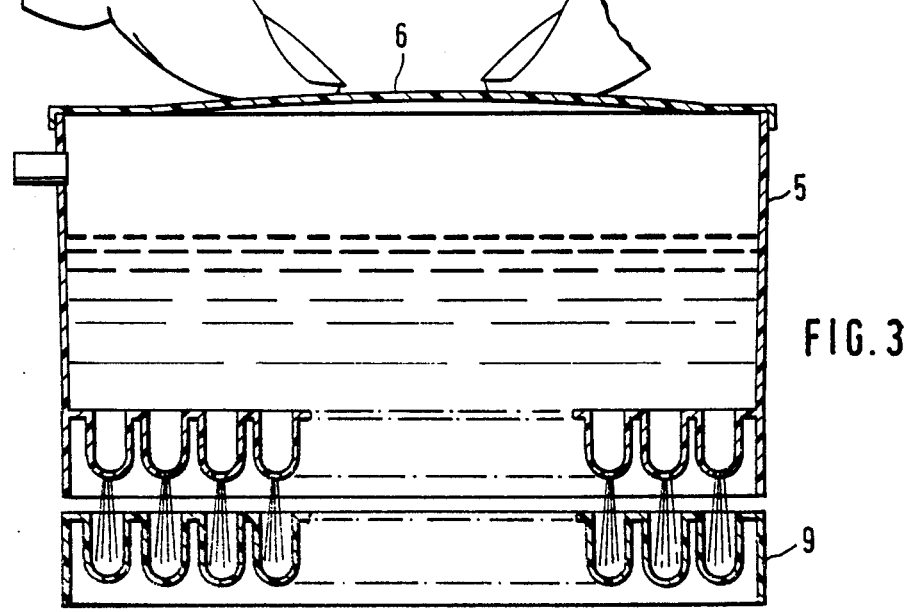
FIG. 3 is a vertical cross-section of the device of FIG. 1 illustrating a mode of use.

FIG. 3 is a view illustrative of how to use the present device, in which reference numeral 9 designates a multi-well plate to be washed.

We claim:

1. A device for forcing liquid into the wells of a multi-well plate, comprising:
   a tank having an interior volume for holding a liquid, said tank including a bottom portion having multiple fine orifices spaced for registry with each of said multiple-wells of said plate, a top portion opposite said bottom portion, and side portions connecting said top portion and said bottom portion;
   means for supplying liquid to the interior of said tank; and
   a pushable surface portion covering a majority of the exterior surface area of said top portion, said pushable surface portion being selectively movable into the interior of said tank for reducing the volume of said tank and thereby forcing liquid contained within said tank through said orifices.

2. A device as set forth in claim 1, wherein said side portions are formed of a hard plastic material.

3. A device as set forth in claim 1, wherein the top portion is detachably connected to the side portions.

4. A device as set forth in claim 1, wherein said supplying means include a supply inlet formed on one of said side portions of said tank.

5. A device as set forth in claim 1, wherein said pushable surface portion is formed of an elastic synthetic resin material.

* * * * *